United States Patent
Marnfeldt et al.

(10) Patent No.: US 8,571,681 B2
(45) Date of Patent: *Oct. 29, 2013

(54) METHOD FOR CONTROLLED SHUTDOWN OF AN IMPLANTABLE MEDICAL DEVICE

(71) Applicant: Boston Scientific Neuromodulation Corporation, Valencia, CA (US)

(72) Inventors: Goran N. Marnfeldt, Valencia, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/873,398

(22) Filed: Apr. 30, 2013

(65) Prior Publication Data

US 2013/0238055 A1   Sep. 12, 2013

Related U.S. Application Data

(63) Continuation of application No. 13/030,848, filed on Feb. 18, 2011, now Pat. No. 8,473,070.

(60) Provisional application No. 61/318,198, filed on Mar. 26, 2010.

(51) Int. Cl.
    *A61N 1/00*  (2006.01)
(52) U.S. Cl.
    USPC .......................................................... 607/63
(58) Field of Classification Search
    USPC ................................... 607/63, 57; 340/870.3
    See application file for complete search history.

(56) References Cited

U.S. PATENT DOCUMENTS

| | | | |
|---|---|---|---|
| 6,516,227 B1 | 2/2003 | Meadows et al. | |
| 6,985,773 B2 | 1/2006 | Von Arx et al. | |
| 7,024,249 B2 | 4/2006 | Weisner et al. | |
| 7,260,436 B2 | 8/2007 | Kilgore et al. | |
| 7,373,200 B2 | 5/2008 | Stubbs et al. | |
| 8,065,019 B2 | 11/2011 | Marnfeldt et al. | |
| 8,165,692 B2 | 4/2012 | Strother et al. | |
| 2005/0043761 A1 | 2/2005 | Connelly et al. | |
| 2008/0300660 A1 | 12/2008 | John | |
| 2009/0024179 A1 | 1/2009 | Dronov | |
| 2010/0179618 A1 | 7/2010 | Marnfeldt et al. | |
| 2010/0328098 A1* | 12/2010 | Stein et al. | 340/870.3 |
| 2011/0112607 A1* | 5/2011 | Zierhofer | 607/57 |
| 2011/0125221 A1 | 5/2011 | Sieracki et al. | |

* cited by examiner

*Primary Examiner* — Robert N Wieland
(74) *Attorney, Agent, or Firm* — Wong, Cabello, Lutsch, Rutherford & Brucculeri, LLP.

(57) ABSTRACT

An improved implantable pulse generator (IPG) containing graceful shutdown circuitry is disclosed. A magnet sensor senses the presence of an emergency shutdown magnet. Output of the magnet sensor is conditioned by a signal conditioning circuit. Output of the signal conditioning circuit is delayed by a delay element before being fed to a power cut-off switch, which cuts-off power to the IPG circuitry. An interrupt signal is routed from before the delay element to the IPG processor as an indicator of imminent shutdown. The processor launches shutdown routine that carries out shutdown operations such as logging the emergency shutdown event, saving and closing open files, saving data from volatile memory to non-volatile memory, etc., before the power cut-off switch is activated upon elapsing of delay provided by the delay element. The magnet sensor, signal conditioning circuit, and delay element are powered separately from the rest of the circuitry of the IPG.

19 Claims, 7 Drawing Sheets

METHOD FOR CONTROLLED SHUTDOWN OF AN IMPLANTABLE MEDICAL DEVICE

CROSS REFERENCE TO RELATED APPLICATIONS

The present application is a continuation of U.S. patent application Ser. No. 13/030,848, filed Feb. 18, 2011 now U.S. Pat. No. 8,473,070 issued Jun. 25, 2013, which was a non-provisional of U.S. Provisional Patent Application Ser. No. 61/318,198, filed Mar. 26, 2010. Priority is claimed to both applications, and both are incorporated herein by reference in their entireties.

FIELD OF THE INVENTION

The present invention relates to improved emergency shutdown circuitry for an implantable medical device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102, 104 couple to the IPG 100 using lead connectors 38a and 38b, which are fixed in a non-conductive header material 36, which can comprise an epoxy for example.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils (more generally, antennas) are generally present in the IPG 100: a telemetry coil 13 used to transmit/receive data to/from an external controller 12; and a charging coil 18 for charging or recharging the IPG's battery 26 using an external charger 50. The telemetry coil 13 is typically mounted within the header 36 of the IPG 100 as shown, and may be wrapped around a ferrite core 13'.

As just noted, an external controller 12, such as a hand-held programmer or a clinician's programmer, is used to wirelessly send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12. The communication of data to and from the external controller 12 is enabled by a coil (antenna) 17.

The external charger 50, also typically a hand-held device, is used to wirelessly convey power to the IPG 100, which power can be used to recharge the IPG's battery 26. The transfer of power from the external charger 50 is enabled by a coil (antenna) 17'. For the purpose of the basic explanation here, the external charger 50 is depicted as having a similar construction to the external controller 12, but in reality they will differ in accordance with their functionalities as one skilled in the art will appreciate.

Wireless data telemetry and power transfer between the external devices 12 and 50 and the IPG 100 takes place via inductive coupling, and specifically magnetic inductive coupling. To implement such functionality, both the IPG 100 and the external devices 12 and 50 have coils which act together as a pair. In case of the external controller 12, the relevant pair of coils comprises coil 17 from the controller and coil 13 from the IPG 100. In case of the external charger 50, the relevant pair of coils comprises coil 17' from the charger and coil 18 from the IPG 100.

When data is to be sent from the external controller 12 to the IPG 100 for example, coil 17 is energized with an alternating current (AC). Such energizing of the coil 17 to transfer data can occur using a Frequency Shift Keying (FSK) protocol for example, such as disclosed in U.S. Patent Publication 2009/0024179. Energizing the coil 17 produces a magnetic field, which in turn induces a voltage in the IPG's coil 13, which produces a corresponding current signal when provided a closed loop path. This voltage and/or current signal can then be demodulated to recover the original data. Transmitting data from the IPG 100 to the external controller 12 occurs in essentially the same manner.

When power is to be transmitted from the external charger 50 to the IPG 100, coil 17' is again energized with an alternating current. Such energizing is generally of a constant frequency, and may be of a larger magnitude than that used during the transfer of data, but otherwise the basic physics involved are similar.

The IPG 100 can also communicate data back to the external charger 50 by modulating the impedance of the charging coil 18. This change in impedance is reflected back to coil 17' in the external charger 50, which demodulates the reflection to recover the transmitted data. This means of transmitting data from the IPG 100 to the external charger 50 is known as Load Shift Keying (LSK), and is useful to communicate data relevant during charging of the battery 26 in the IPG 100, such as the capacity of the battery, whether charging is complete and the external charger can cease, and other pertinent charging variables. LSK communication from an IPG 100 to an external charger is discussed further in U.S. Patent Publication 2010/0179618.

As is well known, inductive transmission of data or power can occur transcutaneously, i.e., through the patient's tissue 25, making it particularly useful in a medical implantable device system. During the transmission of data or power, the coils 17 and 13, or 17' and 18, preferably lie in planes that are parallel, along collinear axes, and with the coils as close as possible to each other. Such an orientation between the coils 17 and 13 will generally improve the coupling between them, but deviation from ideal orientations can still result in suitably reliable data or power transfer.

IPG 100 can comprise circuitry that enables a user or a clinician to shutdown the IPG 100 in case of emergencies. Such emergencies can arise when the IPG 100 malfunctions, undesirably over-stimulates the patient, does not provide stimulation at all, etc. FIG. 3 shows circuitry 302 that is traditionally used in the IPG 100 for emergency shutdown. A user or clinician brings a magnet 300 near the location on the patient's body where the IPG 100 is situated. A magnet sensor 306, such as a reed switch, detects the presence of magnet 300 by way of sensing its magnetic field, and sends an electrical signal (voltage or current) to a signal conditioning circuit 308. The signal conditioning circuit 308 suppresses any stray and transient signals (e.g., reed bounce) received from the magnet sensor 306. Once a sufficient signal indicating presence of magnet 300 is detected, the signal conditioning circuit 308 outputs a signal that opens switch 310. Once switch 310 is open, Rest of the Device (ROD) 312 will be disconnected from battery 26. ROD 312 will typically include all the circuitry responsible for the functioning of the IPG 100. For example, ROD 312 can include the microprocessor, charging circuits, telemetry circuits, stimulation circuits, volatile and non-volatile memory, etc. Upon being disconnected from the battery, these circuits will cease to function.

Although the aim of an emergency stop may be to immediately halt any stimulation being received by the IPG 100, an abrupt shut down like the one depicted in FIG. 3, can have certain disadvantages. For example, any data stored in volatile memory (e.g., RAM) will be lost, which data may include current stimulation program parameters. If the current stimulation parameters were intended to be stored/saved in non-volatile memory (into a stimulation parameter file, for example), an abrupt power loss may prevent the microprocessor from completing the save operation. In other instances it is also possible that the microprocessor is in the process of moving data from volatile memory to non-volatile memory when power loss occurs. This may result in only a partial data store—possibly corrupting the data stored in non-volatile memory.

In other instances it may be beneficial, from an analysis point of view, to record data relevant to the emergency shutdown itself. However, an abrupt shutdown may not allow the microprocessor to log this information into non-volatile memory.

A solution to this problem is provided in this disclosure in the form of an improved emergency shutdown circuit for an IPG 100 or other implantable medical device.

DETAILED DESCRIPTION

The description that follows relates to use of the invention within a spinal cord stimulation (SCS) system. However, it is to be understood that the invention is not so limited, and could be used with any type of implantable medical device system.

Figure 1:
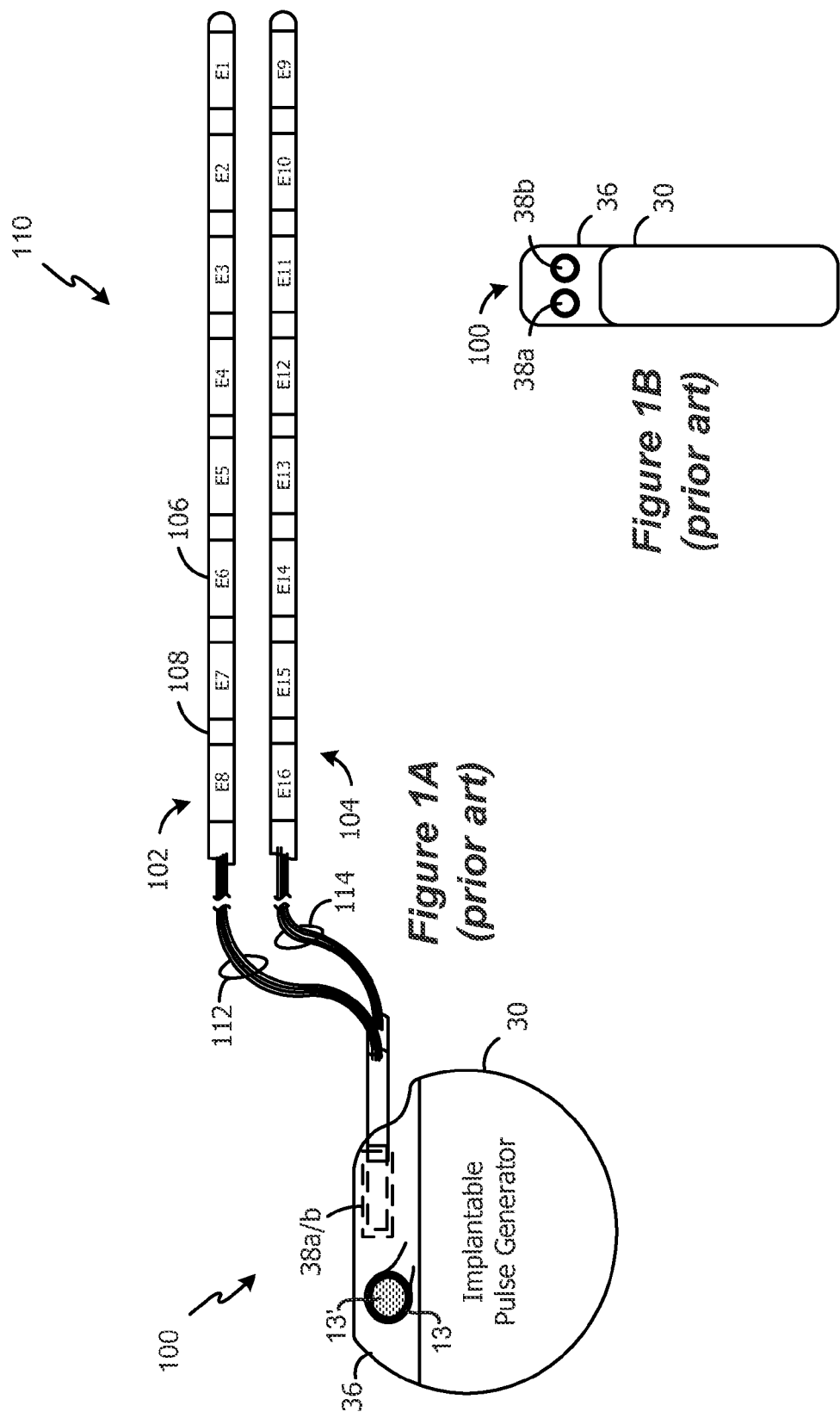
FIGS. 1A and 1B show an implantable medical device, and the manner in which an electrode array is coupled to the IPG in accordance with the prior art.
Figure 2:
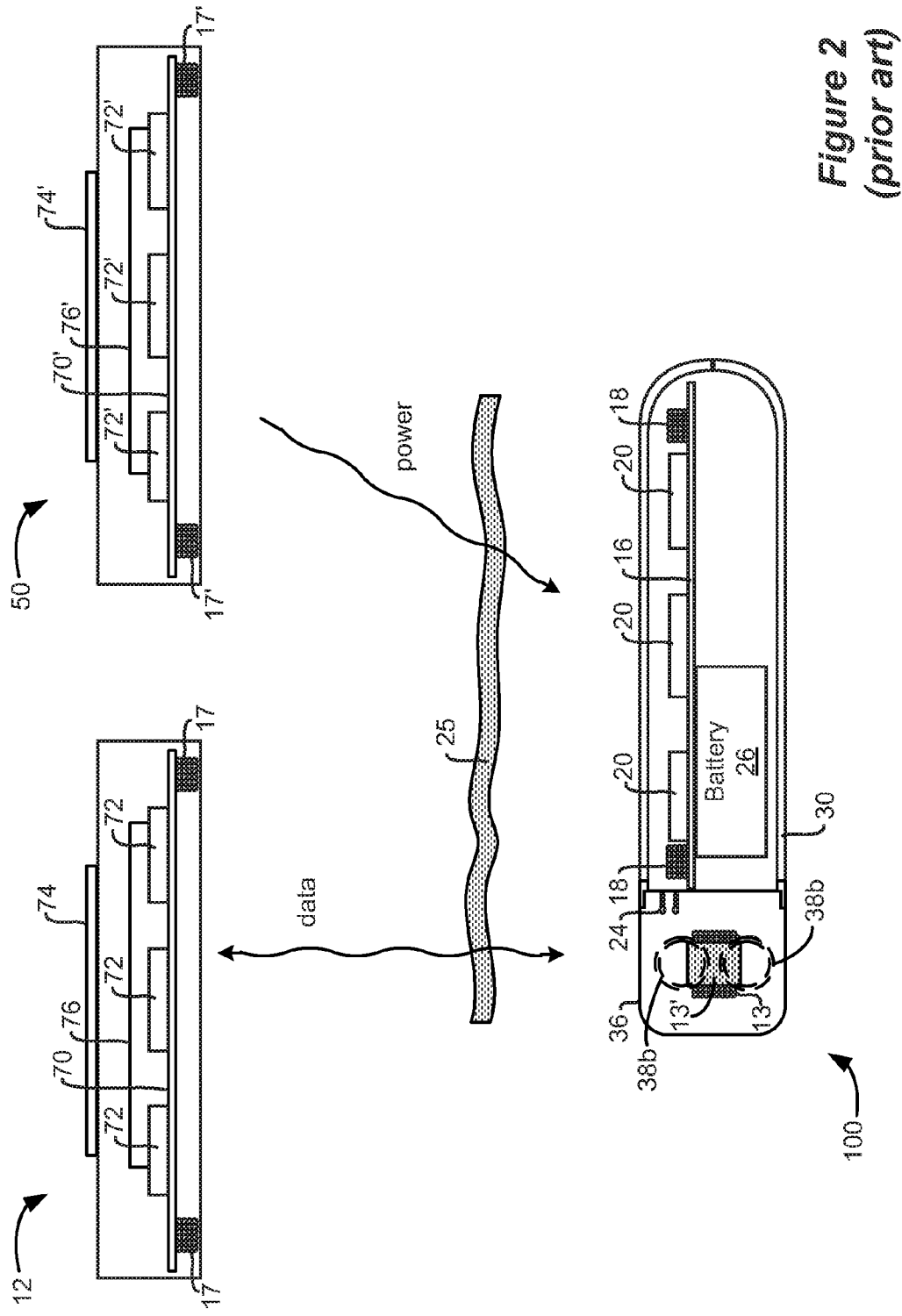
FIG. 2 shows the relation between the implantable medical device, an external controller, and an external charger.
Figure 3:
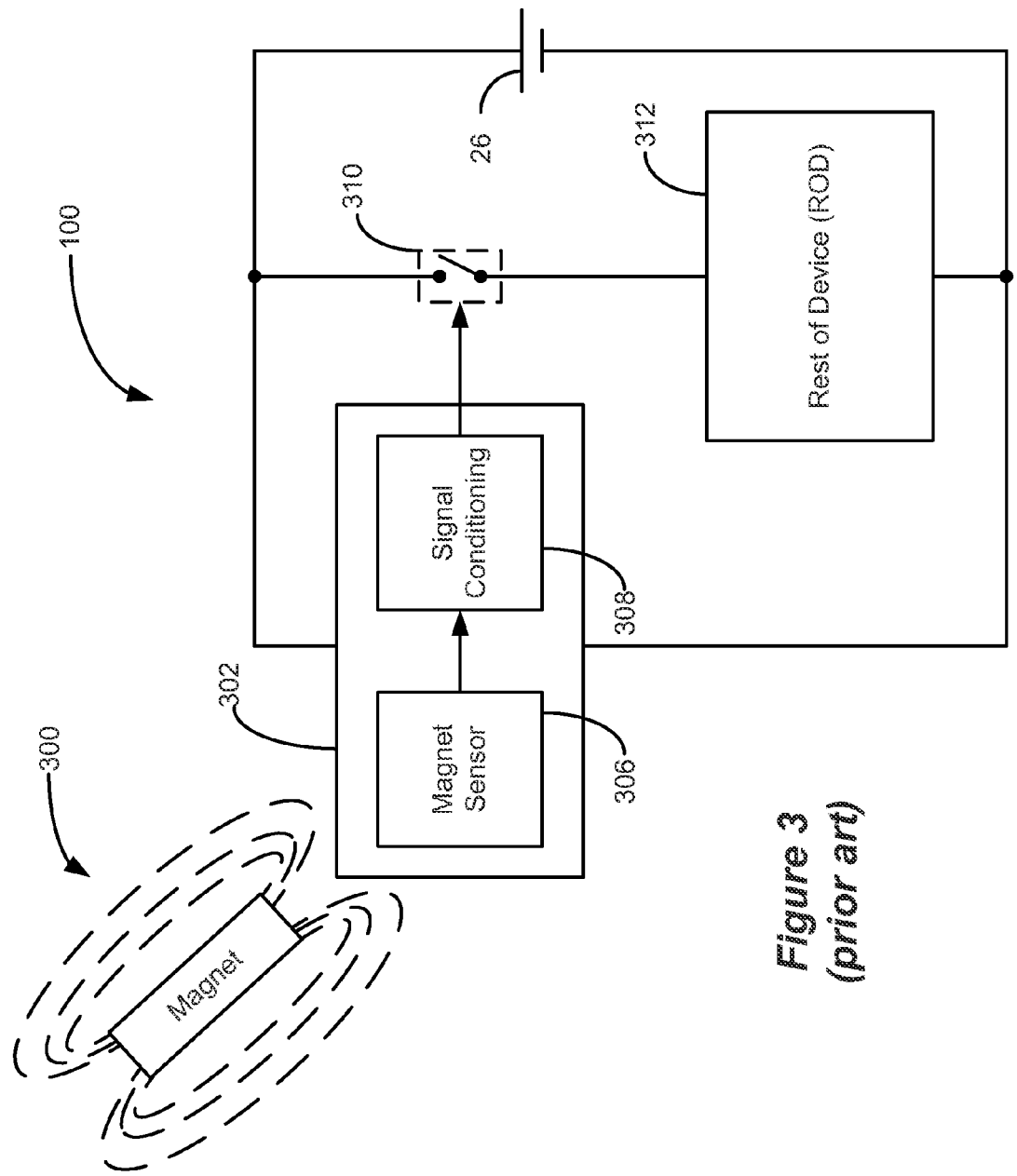
FIG. 3 shows a traditional emergency IPG shutdown circuit in an IPG.
Figure 4:
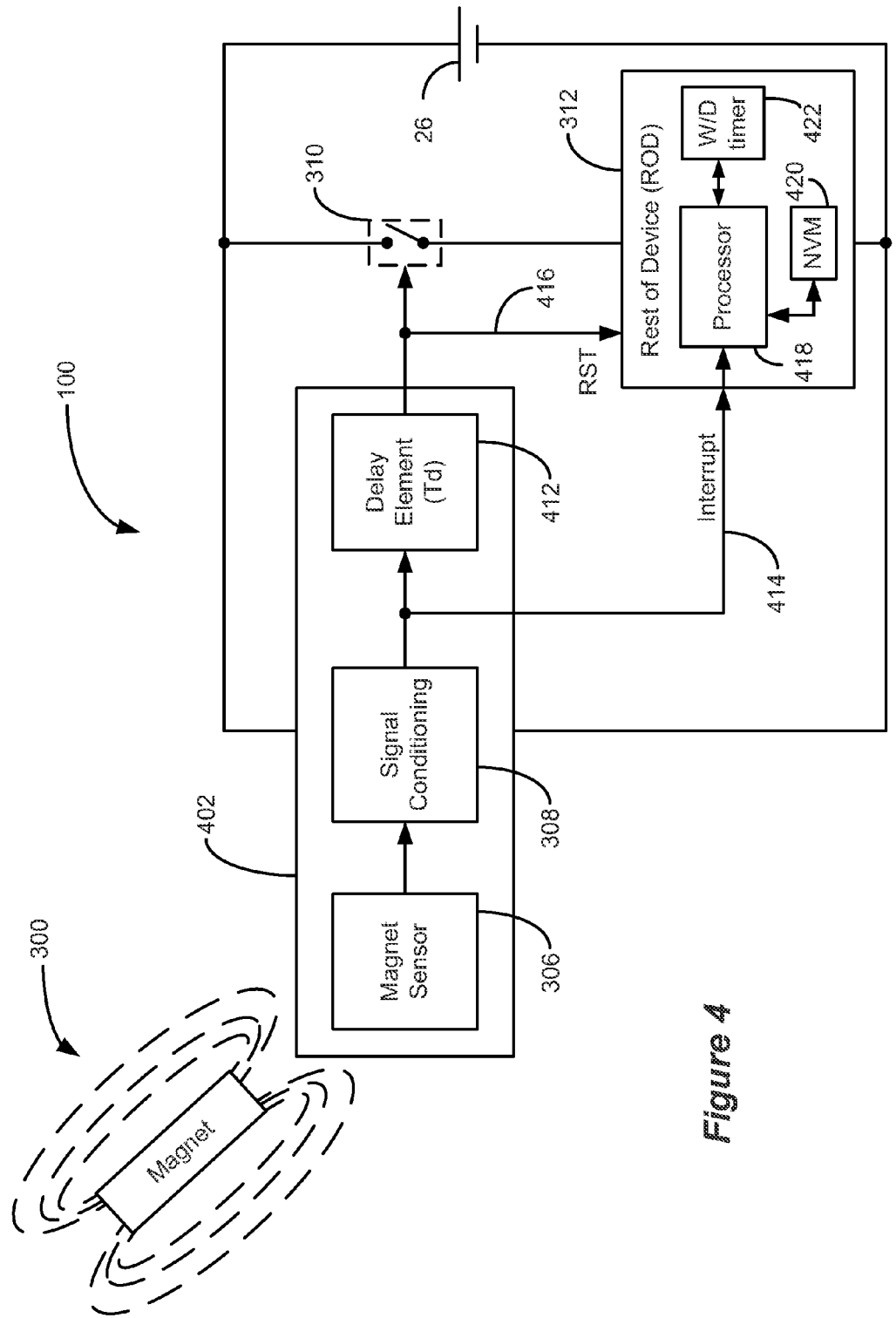
FIG. 4 shows a first embodiment of improved emergency shutdown circuitry for the IPG of FIG. 3 to provide graceful shutdown.

The inventor addresses the problem of data loss during emergency shutdown of the IPG 100 by including a delay element 412 between the signal conditioner 308 and the switch 310 in an improved emergency shutdown circuit 402, as shown in FIG. 4. In contrast with emergency shutdown circuit 302 of FIG. 3, where the output of the signal conditioning circuit 308 is fed directly to the power cut-off switch 310, the emergency shutdown circuit 402 in FIG. 4 instead delays the output of the signal conditioning circuit 308 before it is fed to the power cut-off switch 310. In addition, output of the signal conditioner 308 is provided as an interrupt signal 414 to the ROD 312. As a result, as soon as the signal conditioning circuit 308 outputs signal indicating that magnet 300 has been detected, ROD 312 receives a notification, in the form of the interrupt signal 414, of an imminent emergency shutdown. Interrupt signal 414 is fed to an interrupt pin of processor 418, which can immediately launch a shutdown routine (discussed further below) that allows it to carry out shutdown operations such as logging the emergency shutdown event, saving and closing open files, etc. A timing delay ($T_d$) produced by delay element 412 is selected to provide the processor 418 enough time to complete the launched shutdown routine, which time can vary between applications.

After the elapse of grace-period delay $T_d$, the delay element 412 outputs signal 416. Signal 416 is fed to the input of shutdown switch 310 and a reset pin RST of the processor 418. Upon receiving signal 416, switch 310 (which is normally closed) opens and, as a result, disconnects ROD 312 from battery 26. The emergency shutdown circuit 402, comprising magnet sensor 306, signal conditioning circuit 308, and the delay element 412, is powered separately from the ROD 312. Furthermore, emergency shutdown circuit 402 may be implemented on a separate substrate than the one on which ROD 312 is implemented. This reduces system faults that may occur in the ROD 312 from affecting the emergency shutdown circuit 402.

Figure 5:
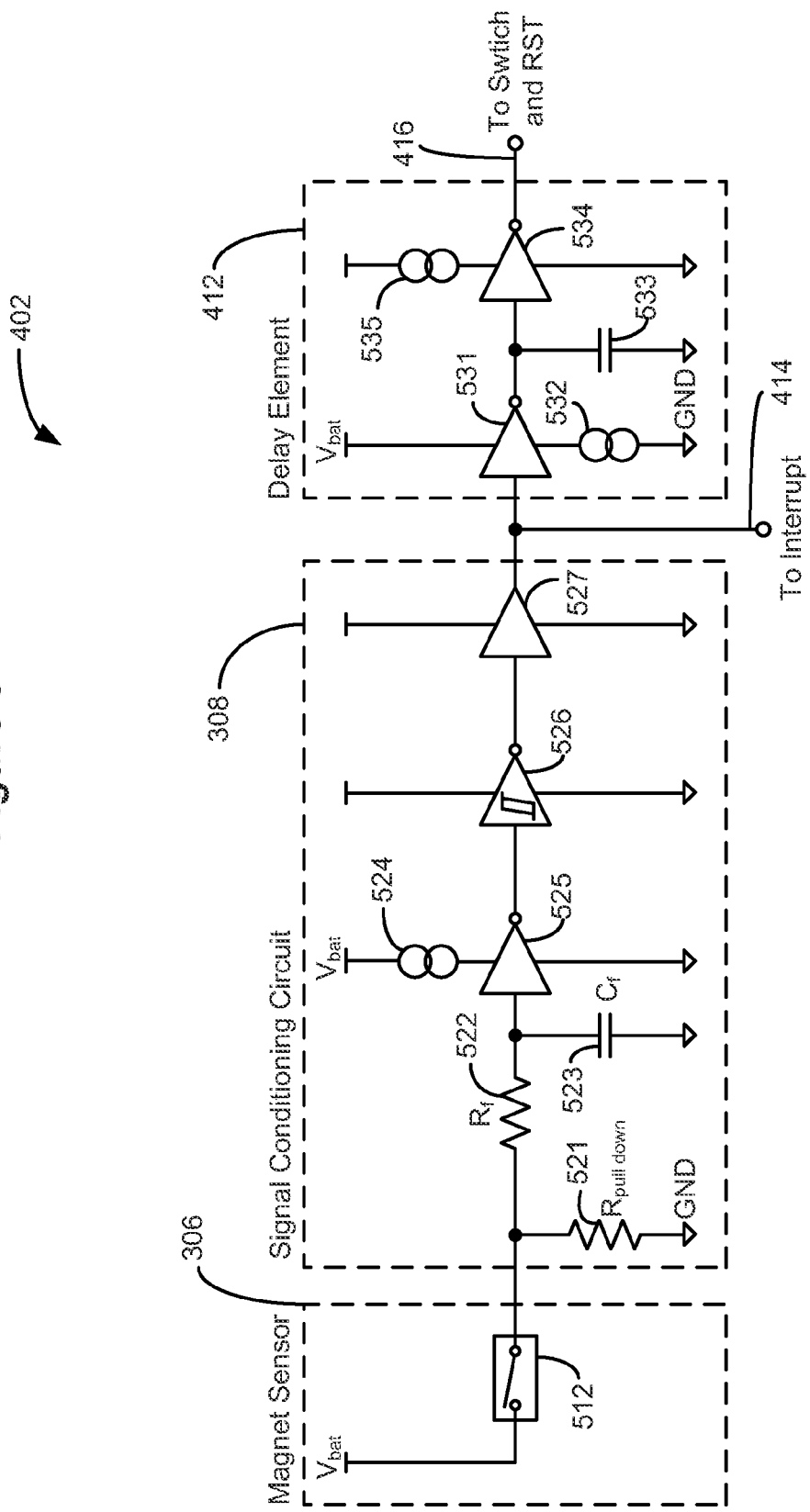
FIG. 5 shows a detailed exemplary circuit diagram of the emergency shutdown circuitry of FIG. 4.

FIG. 5 shows a detailed exemplary circuit diagram of emergency shutdown circuit 402. In default state—when no magnetic field is sensed by the magnet sensor 306—the output of the magnet sensor is pulled low by the pull down resistor $R_{pull\ down}$ 521. Therefore, the output 414 of the signal conditioning circuit 308 is low. Note that the output 414 of the signal conditioning circuit 308 is coupled to an interrupt input of the processor (418, FIG. 4). It is assumed that the processor 418 activates an interrupt routine only when the interrupt input of the processor is at logic high value. Therefore, in the default state, the processor is not interrupted. Furthermore, by virtue of inverters 531 and 534, the output 416 of the delay element 412 is also logic low and the capacitor 533 is fully charged. Therefore, shutdown switch 310 remains closed, keeping ROD 312 connected to battery 26. In other words, without the detection of an emergency stop by way of magnet 300, ROD 312 continues to receive power.

As stated before, when an emergency shutdown is needed, magnet 300 is brought near the IPG 100. Magnet sensor 306 senses the approach of magnet 300. Magnet 300 is typically a permanent magnet that produces a magnetic field that is considerably larger than the earth's magnetic field (~0.5 gauss). Magnet sensor 306 is preferably designed such that it produces a null output when placed in only the earth's magnetic field, but produces an output when placed in the magnetic field produced by magnet 300. Several types of magnetic field sensors 306 can be used, for example, reed switches, InSb magnetoresistors, Hall devices, GMR sensors, etc.

As an example, FIG. 5 shows a reed switch 512 being used as magnet sensor 306. One end of the reed switch 512 is connected to the supply voltage $V_{bat}$, while the other end is connected to pull down resistor $R_{pull\ down}$ 521. The pull down resistor $R_{pull\ down}$ 521 maintains the voltage at the output of the magnet sensor 306 to a voltage that is approximately equal to GND. The reed switch 512 includes a pair of flexible, ferromagnetic contacts, which get magnetized by the presence of the magnetic field of magnet 300. This magnetization causes the contacts to attract each other and close the circuit. This results in the output of the magnet sensor 306 to be pulled high.

It is not unusual for the output of the magnetic sensor 306 to toggle or fluctuate between high and low values. This can be caused due to reed bounce within the reed switch 512, or by erratic movement of the magnet 300. Fluctuations can also be caused by magnets other than magnet 300, such as magnets in DC motors and other electrical devices that the patient may commonly encounter in close proximity around the house or workplace. It is not desired that such fluctuations be interpreted as an actual emergency shutdown condition. Therefore, a low pass filter, formed by resistor $R_f$ 522 and capacitor $C_f$ 523, within the signal conditioning circuit 308 is connected to the output of the magnet sensor 306, which low pass filter filters the output of the magnet sensor 306 before it is fed to inverter 525. The frequency response of the low pass filter can be adjusted by the values of $R_f$ and $C_f$. Although a passive filter formed by resistor $R_f$ 522 and capacitor $C_f$ 523 has been shown in FIG. 5, a person skilled in the art will appreciate that active filters designed using components such as transistors, operational amplifiers, etc., can also be used.

Inverter 525, Schmitt trigger 526, and buffer 527 digitize the filtered output of the magnet sensor 306. Once the filtered output of the magnet sensor 306 reaches a sufficiently high value, the output of the inverter 525 goes low. The input to inverter 525, i.e., the output of magnet sensor 306, may transition from low to high relatively slowly by virtue of the passive filter. This can cause excessive current draw through the inverter 525, which is typically (but not necessarily) implemented using CMOS technology. In particular, the "crowbar current" experienced during a CMOS logic state transition can be exacerbated by the filter. To limit this crowbar current, a current source 524 is placed in series with the supply voltage ($V_{bat}$) of the inverter 525.

Figure 6A:
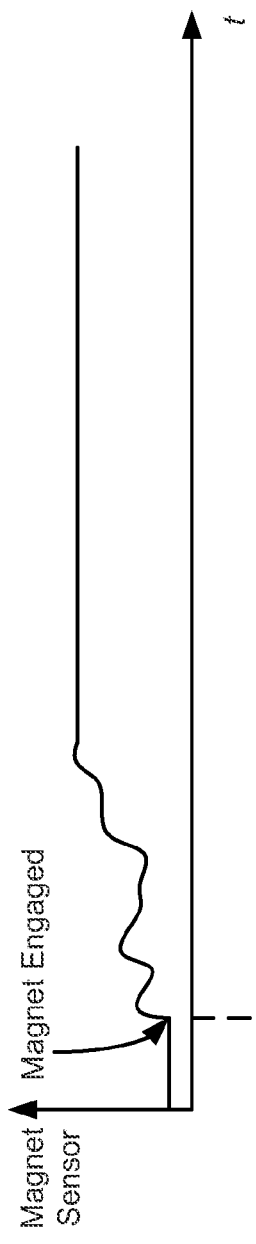
FIGS. 6A-6D show timing diagrams of various signals of the circuits shown in FIGS. 4 and 5.
Figure 6B:
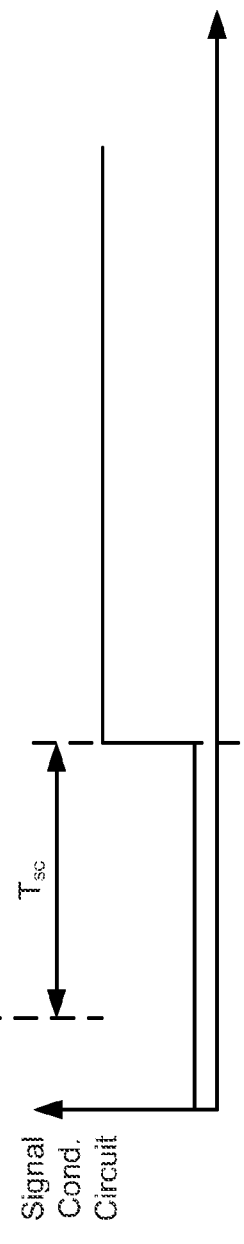

Output of the inverter 525 is fed to an inverting Schmitt trigger 526, which will quickly transition from low to high even if the output of the inverter 525 changes from high to low relatively slowly. The output of the Schmitt trigger 526 is fed to the input of buffer 527, which follows the input to the trigger 526. The operation of signal condition circuit 308 can be seen in FIGS. 6A and 6B, which respectively show the unfiltered output of the magnet sensor 306, and the digitized output of the signal condition circuit 308. Time $T_{sc}$ denotes the time taken from the moment the magnet 300 is first sensed by the magnet sensor 306 to the moment the output of signal condition circuit 308 goes high, and essentially represents the time taken to appropriate condition the signal. $T_{sc}$ would normally be significantly less than the grace-period delay $T_d$, and may be included as part of the grace period delay.

Output of signal conditioning circuit 308 is fed to two locations—as an interrupt signal 414 to processor 418 and to the delay element 412. The interrupt 414 to the processor 418 starts an interrupt service routine within the processor 418 that carries out controlled shutdown of the IPG 100. The delay element 412 delays the output from the signal conditioning circuit 308 from opening switch 310 by an amount $T_d$, which is designed to provide the processor 418 sufficient time to carry out the required shutdown operations. The shutdown operation of the processor 418 is described with further detail below with respect to FIG. 7.

Figure 6C:
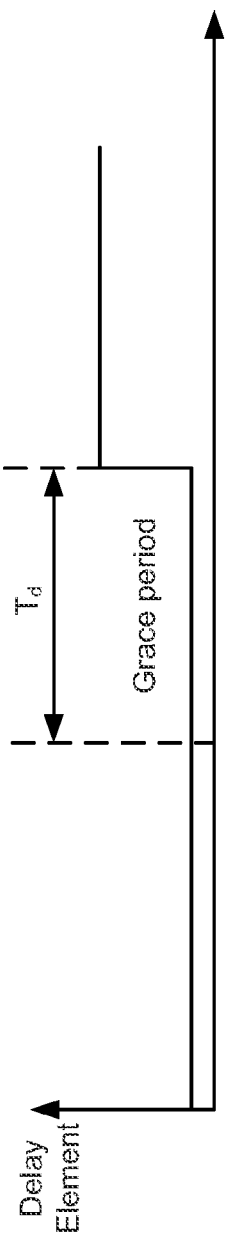

The delay element 412 includes inverter 531, delay capacitor 533, and inverter 534. When input of inverter 531, which is connected to the output of signal conditioning circuit 308, changes from low to high, the output of inverter 531, changes from high to low. Note that in default state (with no emergency shutdown) the delay capacitor 533 is fully charged to a high state. Therefore, the charge stored in the delay capacitor is drained to ground GND via the n-MOS transistor (not shown) of inverter 531 and current source 532. The amount of time it takes for the output of the inverter 531 to go from high to low depends upon the amount of time it takes to discharge delay capacitor 533, which time depends upon the size of delay capacitor 533, the size of the n-MOS transistor of the inverter 531 and the value of the current source 532. Having a small size n-MOS transistor and a small value of current source 532 can increase the time it takes to discharge capacitor. Discharge time can also be increased by increasing the size of the delay capacitor 533. When the output of the inverter 531 begins to change from high to low, the output of the inverter 534 begins to change from low to high. In case of inverter 534, capacitance at the output of the inverter 534 is charged via the p-MOS transistor (not shown) of the inverter 534 and current source 535. Capacitance at the output of inverter 534 will predominantly be interconnect capacitance. The amount of time required to charge this interconnect capacitance depends upon the value of the current source 535 and the size of the p-MOS transistor of inverter 534. Decreasing the value of the current source 535 can increase the discharge time. Similarly, decreasing the size of the p-MOS transistor will increase the discharge time. In any event, these various values set the total delay $T_d$ offered by the delay element 412. After delay $T_d$, the output of the delay element 412 goes high as shown in FIG. 6C. At this time, the shutdown switch 310 is opened, disconnecting the ROD 312 from the battery 26.

Figure 7:
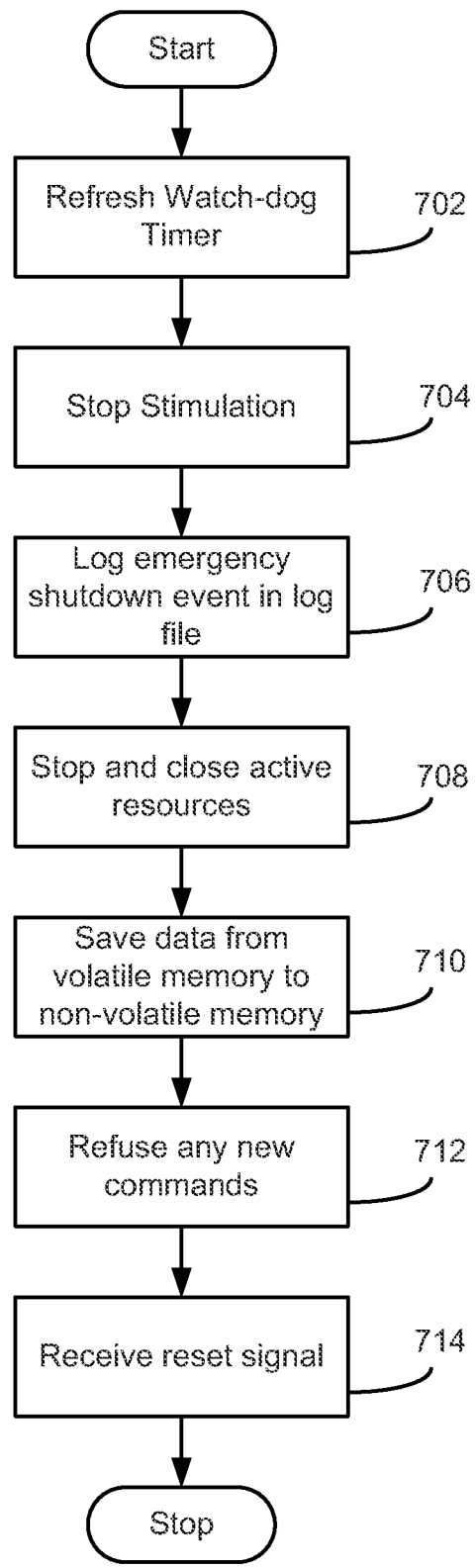
FIG. 7 shows a flowchart depicting shutdown operations performed by the IPG.

As stated earlier, output of signal conditioning circuit 308 is fed as an interrupt signal 414 to processor 418. Processor 418 may have one or more interrupt pins. Preferably, the interrupt signal 414 is connected to a non-maskable interrupt (NMI) pin of the processor 418 so that the interrupt signal 414 is never ignored. Upon receiving an interrupt, the processor 418 launches an interrupt service routine (ISR), such as a shutdown routine, associated with that interrupt pin, which ISR is illustrated in FIG. 7. This ISR carries out shutdown operations such as logging the emergency shutdown event, saving and closing open files, etc., before time $T_d$ has lapsed, i.e., before the ROD 312 is disconnected from its power supply.

In step 702, processor 418 refreshes a watch-dog timer 422 (FIG. 4). The watch-dog timer 422 resets the processor 418 upon completion of a predetermined time interval, and can be implanted as a counter. For example, a down counter with initial count of FFFF will reset the processor 418 when it reaches 0000. Processor 418 periodically refreshes the watch-dog timer by resetting the counter before it reaches 0000. Non-servicing of the watch-dog timer before it reaches 0000 can serve as an indication of a fault condition or state. Therefore, the resetting of the processor 418 by the watch-dog timer 422 can bring the processor back to normal operation. In step 702, the processor resets the watch-dog timer 422 right at the outset of the shutdown routine so that the processor 418 can dedicate maximum available time in carrying out shutdown operations. Note that although the watch-dog timer 422 in FIG. 4 is shown as a separate entity from the processor 418, it is not uncommon for processors 418 to include a watch-dog timer 422.

In step 704 processor 418 stops any stimulation given to the patient, i.e. ceases any therapeutic operation being performed by the implantable medical device. Alternatively, operation of the implantable medical device may not cease entirely, but instead may enter a different mode safer for the patient. For example, in a neurostimulator, initiation of the shutdown routine may simply reduce the magnitude of the stimulation settings to levels known to be conservatively safe for even the most sensitive patient.

In step 706, processor 418 logs the emergency shutdown event in a log file stored in non-volatile memory 420 (FIG. 4). This includes various status data which can be telemetered back to the external controller 12 for further analysis. Such status data can include operation parameters such as current battery voltage, $V_{bat}$, stimulation status data, time stamps, including the time when the emergency shutdown event occurred, etc. The time stamps can be derived from an internal IPG clock (not shown). In some cases, the internal IPG clock may be inaccurate, although the technique disclosed in U.S. Patent Publication 2010/0125316 can help in this regard.

In step 708, processor 418 stops and closes any open or active resources such as file systems. This can entail closing log files, stimulation files that contain stimulation data, or system files required for the operation of the processor 418. By systematically closing open or active files, corruption or loss of data associated with an abrupt shutdown can be reduced or avoided. Closing files can also include saving data associated with the open files into non-volatile memory 420.

Figure 6D:
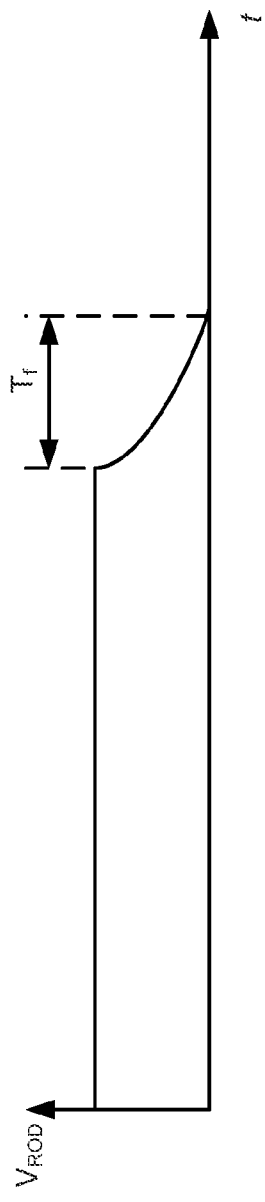

In step 710, processor 418 stores any remaining but required information from volatile memory (not shown in FIG. 4) to non-volatile memory 420. The processor 418 then enters a state where it does not accept any additional commands (step 712). This is because the external controller 12 or an external charger 50 may be unaware that the IPG 100 is undergoing an emergency shutdown, and may continue to send commands and or instructions. Because the IPG 100 is being prepared for shutdown, any such commands or instructions are ignored. Processor 418 stays in step 712 until the delay time $T_d$ elapses and the processor 418 receives the reset RST signal 416 from the delay element 412 (step 714), which signal also opens switch 310 to disconnect ROD 312 from the power supply (e.g., battery 26). As shown in FIG. 6D, at this time, the power supply voltage at the ROD will begin to exponentially decay, taking a time $T_f$ to complete, which time may be abrupt. However, because the ISR is designed to have completed during $T_d$, the IPG 100 is unaffected by this fall off in the power supply voltage.

In cases where the processor 418 has been rendered non-operational, the processor 418 will be incapable of executing the shutdown routine described. In such cases, the ROD 312 is still disconnected from the power supply, and the reset RST signal 416 is still given to the processor 418 after delay $T_d$.

Magnet 300 can be removed from the proximity of the IPG 100 to allow the IPG 100 to return to normal operation. For example, when magnet 300 is moved away from the IPG 100, reed switch 512 will open and disconnect the output of the magnet sensor from $V_{bat}$. As a result, the output of the magnet sensor 306, and ultimately interrupt signal 414, are both pulled low indicating that an emergency shutdown state no longer exists. Note that at this time the ROD 312 is still disconnected from the power supply. Once the interrupt signal 414 begins to transition low, the reset signal 416 to the processor 418 will also go low and switch 310 closed after some delay through the delay element. (Note that the high-to-low transition may be differently delayed from the low-to-high transition delay of Td if the circuitry within the delay element 412 is not balanced). Processor 418 and the ROD 312 may then enter initialization and restore normal operation of the IPG 100.

Although the improved emergency shutdown circuitry is disclosed as being activated upon receipt of a magnetic field from a simple magnet, applications of the technique are not so limited. Instead, the sensor can generically sense any shutdown signal wirelessly communicated from any source external to the implantable medical device. For example, the shutdown signal may comprise a shutdown command telemetered to the sensor 306 from the external controller 12 or external charger 50, with the sensor 306 in this case comprising a coil or other antenna. Even if such relatively-sophisticated means are used to signal the IPG to shutdown, the improved circuitry 402 can still operate to shutdown the IPG in a controlled and graceful manner.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
    sensor circuitry configured to produce a sensor output upon wirelessly detecting an external signal;
    delay circuitry configured to produce a delayed output a delay time after the sensor output is produced;
    implant circuitry configured to perform an action upon receipt of the sensor output, wherein the action is configured to be completed within the delay time; and
    a switch configured to disconnect a power supply from the implant circuitry upon receipt of the delayed output.

2. The implantable medical device of claim 1, wherein the external signal comprises a magnetic field produced by a magnet.

3. The implantable medical device of claim 1, wherein the external signal comprises a telemetry signal.

4. The implantable medical device of claim 1, wherein the action comprises stopping therapeutic operation of the implantable medical device.

5. The implantable medical device of claim 1, wherein the action comprises initiating a shutdown routine.

6. The implantable medical device of claim 1, wherein the action comprises closing open or active files in the implant circuitry.

7. The implantable medical device of claim 1, wherein the implant circuitry comprises a counter, and wherein the action comprises resetting the counter.

8. The implantable medical device of claim 1, wherein implant circuitry is further configured to perform operations, and wherein the action comprises stopping at least some of operations being performed in the implant circuitry.

9. The implantable medical device of claim 8, wherein one of the stopped operations comprises receiving commands from an external controller configured to communicating with the implantable medical device.

10. The implantable medical device of claim 1, wherein the implant circuitry comprises a non-volatile memory, and wherein the action comprises writing data to the non-volatile memory.

11. The implantable medical device of claim 10, wherein the data comprises data regarding the status of the implantable medical device.

12. The implantable medical device of claim 10, wherein the data comprises at least one time stamp.

13. The implantable medical device of claim 10, wherein the data comprises an indication of an emergency shutdown.

14. The implantable medical device of claim 1, wherein the sensor circuitry comprises conditioning circuitry configured to condition the sensor output.

15. The implantable medical device of claim 1, wherein the power supply comprises a battery.

16. The implantable medical device of claim 1, wherein the delay time is fixed.

17. The implantable medical device of claim 1, wherein the delay circuitry comprises a capacitor configured to set the delay time.

18. The implantable medical device of claim 1, wherein the implant circuitry comprises a processor.

19. The implantable medical device of claim 1, wherein the implant circuitry comprises a stimulation circuit configured to stimulate a patient's tissue.

* * * * *